United States Patent [19]

Freeman

[11] Patent Number: 4,642,112
[45] Date of Patent: Feb. 10, 1987

[54] ARTIFICIAL EYE LENSES

[75] Inventor: Michael H. Freeman, Denbigh, Wales

[73] Assignee: Pilkington P.E. Limited, United Kingdom

[21] Appl. No.: 368,362

[22] Filed: Apr. 14, 1982

[30] Foreign Application Priority Data

Apr. 29, 1981 [GB] United Kingdom ............... 8113149
Jun. 10, 1981 [GB] United Kingdom ............... 8117709
Dec. 23, 1981 [GB] United Kingdom ............... 8138854

[51] Int. Cl.⁴ .......................... A61F 2/16; G02C 7/04; G02C 7/10
[52] U.S. Cl. .................................. 623/6; 351/160 R; 351/161; 351/162; 351/163
[58] Field of Search .................... 3/13; 351/160–163; 623/6, 5

[56] References Cited

U.S. PATENT DOCUMENTS

| 3,339,997 | 9/1967 | Wesley | 351/161 |
| 3,794,414 | 2/1974 | Wesley | 351/161 |
| 4,073,579 | 2/1978 | Deeg et al. | 351/169 |
| 4,206,518 | 6/1980 | Jardon et al. | 3/13 |
| 4,210,391 | 7/1980 | Cohen | 351/161 |
| 4,377,329 | 3/1983 | Poler | 3/13 X |
| 4,402,579 | 9/1983 | Poler | 3/13 X |

OTHER PUBLICATIONS

The Leiske Physioflex Style 10 Anterior Chamber Lens, Surgidev Corp., 1421 State Street, Santa Barbara, Calif., 93101, Jan. 4, 1981.

Primary Examiner—Ronald L. Frinks
Attorney, Agent, or Firm—F. Eugene Davis, IV; Mark P. Stone

[57] ABSTRACT

A contact lens has a transmission hologram which provides diffractive power on a wavelength and/or amplitude selective basis whereby light from near and distant objects can be focussed on the retina of a presbyopic wearer. Similarly an implant lens can have a transmission hologram to correct for non-accommodative vision. The invention is particularly useful in providing an artificial eye lens with a bi-focal action without need for distinct near and far vision zones.

24 Claims, 8 Drawing Figures

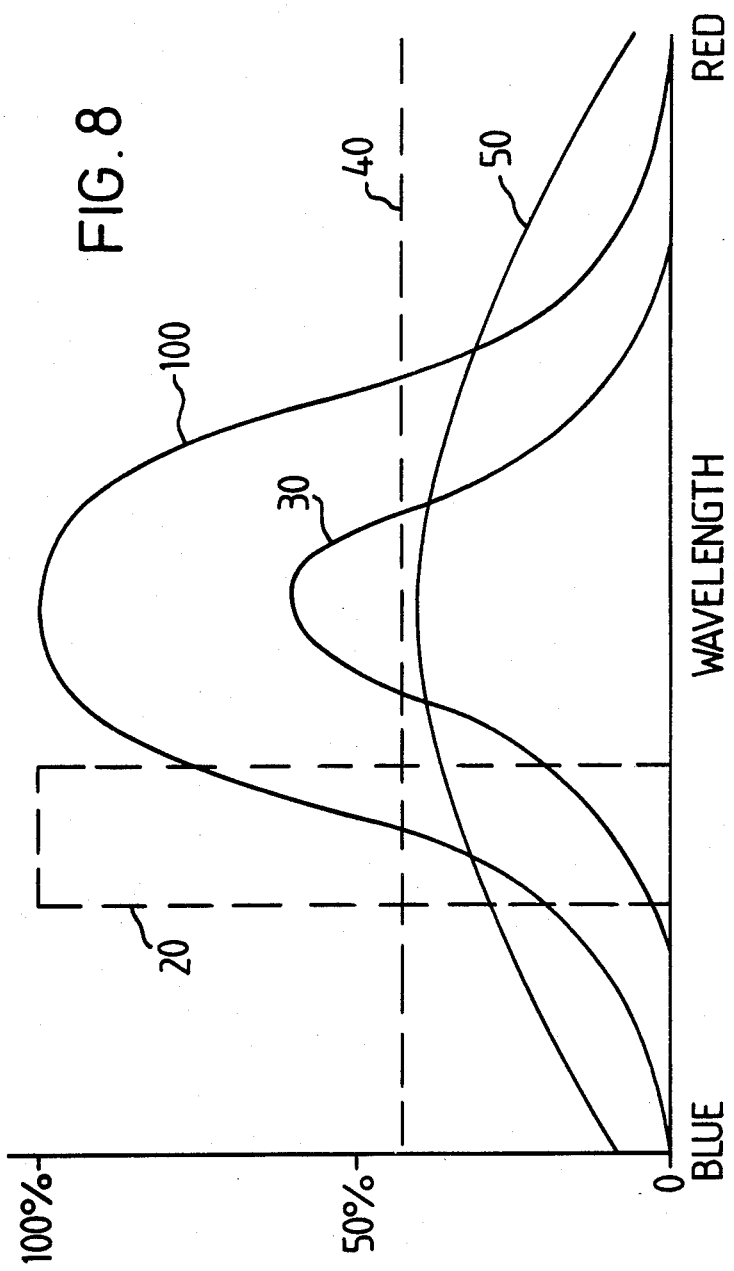

ARTIFICIAL EYE LENSES

BACKGROUND OF THE INVENTION

This invention concerns improvements in or relating to artificial eye lenses and relates more particularly, but not exclusively, to bi-focal artificial eye lenses. By the term "artificial eye lens" is meant an artificial lens which in use is disposed against the eye or within the eye. Thus one particular type of artificial eye lens is a contact lens which is used against the eye to assist the action of the natural eye lens, and another is an implant lens which is inserted in the eye to replace the natural eye lens.

There have been various prior proposals for contact lenses including bi-focal contact lenses. Generally a bi-focal lens is required to provide a certain power for far vision and a different, usually greater (more positive), power for near vision, the additional power for near vision sometimes being referred to as a "near-add" value which is usually expressed in dioptres. Normally the bi-focal effect is achieved by the use of different curvatures and/or materials of different refractive indices for different parts of the lens, so as to provide the required different powers in the respective different parts, which are often referred to as the far and near zones. Thus the user sees far objects by means of light transmitted through the far zone part of the lens and near objects by means of light transmitted through the near zone part of the lens. It has also been proposed (in U.S. Pat. No. 3,339,997) effectively to utilize the chromatic aberration of the eye and to provide far and near zones which transmit different wavelengths of light. Specifically different parts of the lens providing the far and near zones are made of differently coloured filtering material.

This proposal claims the advantage that the same curvature can be used for the far and near zones, the effective power difference being provided by the different wavelengths transmitted. However, the amount of power difference which can be achieved in this manner is limited. In realistic terms near-add values of up to about one dioptre can be provided by selection of appropriate colours and, although in theory greater values are possible by use of violet for the near zone and red for the far zone, there is the practical problem that the colours are darker and less light enters the eye. Further, such a lens still requires distinct parts providing the near and far zones.

Implant or intra-ocular lenses are designed to be inserted within the eye by an ophthalmological surgeon after the removal of the natural lens for reasons of its pathological conditions such as cataract. Whereas the natural lens may be deformed by the ciliary muscle to effect accommodation, that is the ability of the eye to focus on objects at different distances, the implant lens is both rigid and not connected to the ciliary muscle. The eye thus treated, while giving better vision than previously, is totally lacking in accommodation, a situation that applies to the natural lens in later life due to the hardening of the natural lens, a condition known as presbyopia.

SUMMARY

Broadly according to the present invention there is provided an artificial eye lens having diffractive power, and more particularly an artificial eye lens having a transmission hologram which provides diffractive power.

The diffractive power, equivalent to lens power, may be over a particular wavelength band or bands so as to have a selective focussing action on light within that wavelength band or bands. Light of other wavelengths can be transmitted through the hologram undeviated by the hologram. The diffractive power may be of less than 100% efficiency such that a proportion of incident light of a relevant wavelength is diffracted while the remainder of the incident light of that wavelength is undeviated by diffraction. The artificial eye lens may have some diffractive power over all or substantially all of the visible spectrum, but there may be different efficiencies, e.g. ranging from about 20% to about 40%, over different parts of the visible spectrum.

An artificial eye lens in accordance with the invention can have a focussing action on that porportion of the incident light it diffracts to which the other incident light is not subject. The lens can thus, for example, have a bi-focal action. The diffractive power may be additive to (or subtractive from) basic refractive power of the artificial eye lens. Thus a bi-focal artificial eye lens in accordance with the invention may have a basic power, e.g. for far vision, provided by the shape, curvature and material of the lens, and a different power, e.g. a greater power for near vision, through the diffractive power provided in particular by a transmission hologram. The hologram may be provided over the full area, or the full visually used area, of the artificial eye lens and thus, with a bi-focal lens, can avoid need for distinct near and far vision zones.

In principle the difference in power provided by the diffractive power, which would usually be additive to the basic power, can be any desired number of dioptres. In practice the power of the transmission hologram is preferably up to about four dioptres so that a bi-focal artificial eye lens in accordance with the invention may for example have a near-add value between 0 and +4 dioptres.

The hologram may be formed in a layer of the artificial eye lens. Alternatively the hologram may be formed actually in, or as a surface variation on, the bulk material of the artificial eye lens.

In the case of a contact lens the hologram may be formed in a surface layer of photographic material, such as dichromated gelatin, such layer normally being on the surface of the lens which in use is remote from the eye. Alternatively the hologram may be formed actually in the bulk material of the contact lens. In general hologram formation in a surface layer is more appropriate with a hard contact lens while hologram formation in the bulk material is appropriate with a soft contact lens or a hard contact lens.

In the case of an implant lens the hologram may be formed actually in the bulk material of the lens, or may be formed in a layer of photographic material, such as dichromated gelatine, such layer normally being located within the implant lens, e.g. sandwiched between parts thereof.

The hologram may be optically generated by use of active and reference light beams, e.g. from a laser, directed at the artificial eye lens from locations, e.g. effectively providing point sources, appropriate to the power required in the resultant hologram. Such beams produce interference fringes, the vergence difference between the active and reference beams being equal to the required power in the reultant hologram. In practice the reference beam may be collimated, e.g. effectively originating from a location at infinity, the power of the hologram then being equal to the divergence of the active beam. Alternatively, active and reference beams originating from locations at respective finite distances providing the required vergence difference may be employed. The originating locations of the beams may be optically generated rather than actual and aberrations may be deliberately introduced so that the holographic lens is a better match to the requirements of the eye. The effective field of view of the holographic lens may be modified by the shape and depth of the interference fringes. In order to include the fovea the overall field of view of the hologram may be made sufficiently large or the active and reference beams may be deliberately off-set to give an off-axis field of view for the hologram. With a contact lens, the lens is preferably shaped or ballasted to locate such an off-axis field of view correctly. With an implant lens, the lens is preferably shaped or marked so that it can readily be inserted so as to locate such an off-axis field of view correctly.

The reference and active beams may be directed at the artificial eye lens from the front or from the rear, allowance being made, or compensation introduced, as necessary for refractive power. Thus the hologram may be generated while the lens is immersed in a liquid. The invention therefore further provides a method of producing an artificial eye lens having diffractive power comprising the steps of immersing the lens in a liquid and directing active and reference light beams at the immersed lens to generate a hologram in the lens.

In the case of a contact lens, if the active and reference beams are directed from the rear, then allowance needs to be made, or compensation introduced, for the refractive power of the posterior surface. In order effectively to remove the refractive power of the contact lens surface from the hologram generation, the lens may be immersed in a liquid whose refractive index matches that of the material of the contact lens. The invention thus further provides a method of producing a contact lens having diffractive power comprising the steps of immersing the contact lens in a liquid whose refractive index matches that of the material of the contact lens, and directing active and reference light beams at the immersed contact lens to generate a hologram in the lens.

In the case of an implant lens, allowance needs to be made, or compensation introduced, for the refractive power of the media in which the implant lens will be operating. In order effectively to remove the refractive power of the implant lens surface from the hologram generation, the lens may be immersed in a liquid of index matching the aqueous and vitreous humours. The invention thus further provides a method of producing an implant lens having diffractive power comprising the steps of immersing the implant lens in a liquid whose refractive index matches that of the material surrounding the implant lens in use, and directing active and reference light beams at the immersed implant lens to generate a hologram in the lens.

Alternatively the artificial eye lens may have a surface relief hologram which may be mechanically generated, for example during moulding of the artificial eye lens by use of a suitably adapted mould surface. The invention thus further provides a method of producing an artificial eye lens comprising the step of moulding the lens using a mould surface adapted to provide a surface relief hologram on the lens.

An artificial eye lens in accordance with the invention may be of any desired curvature, e.g. spherical, aspheric, or toric, and shape, e.g. with or without prism, to suit particular requirements. In the case of a contact lens it may be of the scleral or corneal type.

The bulk material of the artificial eye lens may be tinted.

Although the present invention has particular application to the correction of presbyopic vision by the provision of an advantageous bi-focal contact lens, or non-accommodative vision by the provision of an advantageous bi-focal implant lens, it can find other applications. For example, a contact lens having diffractive power, and in particular a transmission hologram, in accordance with the invention could be used for correction of vision defects other than presbyopia, such as irregular aberrations in the eye, or to improve normal vision by reduction of chromatic aberration. Similarly, an implant lens having diffractive power, and in particular having a transmission hologram, in accordance with the invention could be used for correction of vision defects other than lack of accommodation, such as irregular aberrations in the eye, or to reduce chromatic aberration.

Further, although advantageously the hologram is provided over the full area, or the full visually used area, of the artificial eye lens, it could, if required, be provided over only a desired part of that area. Yet further, if desired an artificial eye lens could be provided with a plurality of separately generated holograms, which may be effectively superimposed, each hologram providing a desired diffractive power, for example over a respective wavelength band or bands, to meet particular circumstances.

BRIEF DESCRIPTION OF THE DRAWINGS

In order that the invention may be better understood, reference will now be made to the accompanying drawings in which, by way of illustration and example:

FIG. 8 is a graphical representation of efficiency of response against wavelength.

DESCRIPTION OF THE PREFERRED EMBODIMENTS

Figure 1:
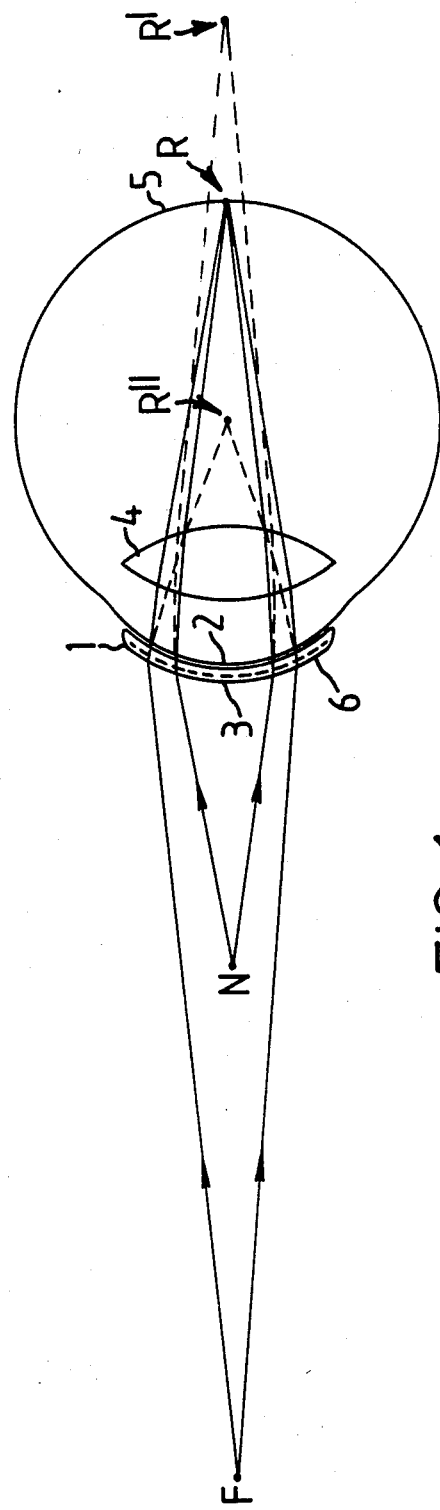
FIG. 1 schematically represents the passage of light through a bi-focal contact lens in accordance with the invention.

FIG. 1 schematically shows an artificial eye lens in the form of a contact lens 1 having a posterior surface 2 of a curvature and shape which in known manner effectively fits the cornea and/or sclera of the wearer, and an anterior surface 3 of shape and curvature related to that of the posterior surface 2 and the refractive index of the material of the lens to provide suitable assistance and correction of the wearer's far vision. It will be understood that the lens is adapted to meet the particular requirements of the wearer so the anterior surface 3 may be of any desired curvature, e.g. spherical or toric, and the lens may be of any desired shape, e.g. with or without prism. For present purposes it is sufficient to consider the lens 1 as providing a basic refractive power appropriate for far vision of the wearer. Thus, light from a far object F is focussed by the contact lens 1 in conjunction with the wearer's natural eye lens 4 to a position R on the retina 5. The wearer can thus look at and see the far object F in focus.

However, since the wearer's vision is presbyopic, the basic lens 1, being adapted to far vision, and the natural eye lens 4 are of insufficient power to effect focussing on the retina of light from a near object N. As shown in broken line, light from such near object N would be focussed at a position R' spaced from and behind the retina 5. To overcome this the contact lens 1 has a transmission hologram, schematically represented at 6, which provides the lens with diffractive power, equivalent to lens power, such that light from the near object N which is diffracted is focussed by the hologram 6 (in conjunction with the basic power of the contact lens 1 and the eye lens 4) on to the retina 5. The wearer can thus look at and see the near object N in focus by means of the light which the hologram diffracts.

As explained later, the hologram may operate on a wavelength selective basis (i.e. such that light within a particular wavelength band or bands is diffracted while light of other wavelengths is transmitted undeviated by the hologram), or on an amplitude selective basis (i.e. such that a proportion or amplitude portion of incident light of whatever wavelength is diffracted while the remainder is transmitted undeviated by the hologram), or on both a wavelength selective and an amplitude selective basis (i.e. such that the hologram operates preferentially over a particular wavelength band or bands but diffracts only a proportion of the incident light within that wavelength band or bands, the remainder of the incident light within that wavelength band or bands and light of other wavelengths being transmitted undeviated by the hologram).

It will be understood that light from the near object N transmitted through the hologram undeviated thereby is focussed at the position R' behind the retina. However, since the position R' is spaced from the retina, the wearer's view of the near object N by way of light diffracted by the hologram is not unduly adversely affected by the undiffracted light. Conversely, when the wearer is looking at the far object F, light therefrom diffracted by the hologram becomes focussed (in conjunction with the action of the basic lens 1 and the natural eye lens 4) at a position R'' spaced from and in front of the retina 5, as shown in broken line. The wearer's focussed view when looking at the far object F is therefore by way of light not diffracted by the hologram 6 and which is therefore transmitted through the hologram undeviated. Since position R'' is spaced from the retina, this far view is not unduly adversely affected by light diffracted by the hologram.

It will be appreciated that the hologram 6 should operate in a manner such as to provide a reasonable balance between the brightness of the far object F as viewed by way of the undiffracted light and the brightness of the near object N as viewed by way of the diffracted light.

It will thus be seen that the lens 1 incorporating the hologram 6 provides a bi-focal effect, the hologram 6 constituting a holographic lens with diffractive power which adds to the basic refractive power of the lens 1 provided by its shape, curvature and material. Although there is in principle no particular limit to the additional power which could be provided by the hologram, preferably it has a power up to about four dioptres thereby giving a near-add value from 0 to +4 dioptres.

Figure 2:
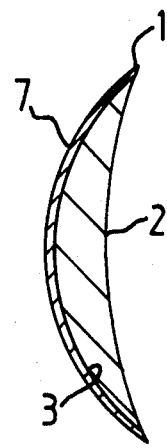
FIG. 2 is a schematic cross-section through a contact lens, FIGS. 3 and 4 schematically illustrate procedures for generating a hologram in a contact lens, FIG. 5 schematically represents the passage of light through a bi-focal implant lens in accordance with the invention.

As shown schematically in FIG. 2, the contact lens 1 may have a surface layer 7 of photographic material, such as dichromated gelatin, on its anterior surface 3, and the hologram 6 may be formed in that surface layer 7. In use the anterior surface 3 is remote from the eye thus avoiding direct contact between the layer 7 and the eye. Formation of the hologram in such surface layer is particularly suitable for a hard contact lens. Alternatively, however, the hologram 6 may be formed actually in the bulk material of the contact lens 1 if the material is suitable for hologram formation by means of an intense light source. Hologram formation in (or as mentioned later by surface relief on) the bulk material is appropriate for hard and soft contact lenses.

The hologram can be optically generated by active and reference beams, for example from a laser, directed at the contact lens effectively from conjugate point sources located so as to provide the required power in the resultant hologram. These light, and preferably laser, beams interfere within the photosensitive material either in the surface layer or the bulk of the contact lens. The interference fringes give areas of light and dark and the light areas, absorbed by the material, cause changes in its refractive index and/or absorption thus forming the hologram. Because of the shape and spacing of these fringes some of the light transmitted in use through the contact lens is diffracted as if the hologram was an additional lens. The power of this additional lens is determined by the origins of the two interfering light beams, and specifically by the vergence difference between them. If, for example, the reference beam is collimated, i.e. effectively originates from a point source located at infinity, it has a divergence of zero. If the active beam originates from a point source located at a finite distance from the contact lens, say 330 mm, then it has a divergence of 3 dioptres. The power of the holographic lens is given by the vergence difference, 3 dioptres, between the two beams. Alternatively active and reference beams originating from point source locations at respective finite distances from the contact lens may be used so long as the vergence difference between them equals the required holographic lens power, i.e. in the bifocal context the required "near-add" value. It will be understood that the originating locations of the active and reference beams may be optically generated, e.g. by use of mirrors or the like, rather than actual. Further, aberrations may be deliberately introduced so that the holographic lens is a better match to the requirements of the eye. These aberrations may be regular as in the case of spherical aberration, coma, astigmatism etc., or may be irregular as best suits the actual eye of a particular wearer.

The bulk material of the contact lens may be tinted.

The effective field of view of the holographic lens may be modified by the shape and depth of the interference fringes. No more than a few degrees is required to give good visual acuity over the fovea but this is not on the axis of the cornea and lens of the eye. The field of view must include the fovea either by increasing, i.e. making sufficiently large, the overall field of view or by deliberately off-setting the active and reference beams to give an off-axis field of view for the hologram preferably with a shaped or ballasted contact lens.

Figure 3:
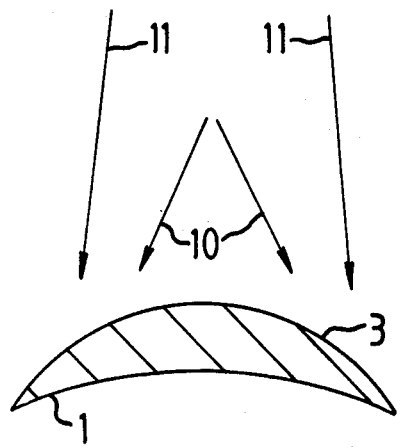

The active and reference beams may be directed at the contact lens from the front, as schematically shown in FIG. 3 in which the beams are indicated at 10 and 11. In this case the refractive power of the anterior surface of the contact lens does not adversely affect the hologram generation and the vergence difference between the beams is maintained.

Figure 4:
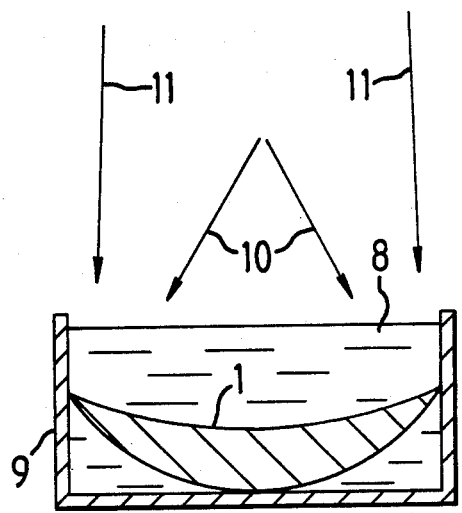

The active and reference beams may alternatively be directed at the contact lens from the rear but in this case allowance should be made, or compensation introduced, for the refractive power of the posterior surface. In order effectively to remove the refractive power of the contact lens surface from the holographic generation procedure, the contact lens 1 can, as schematically shown in FIG. 4, be immersed in a liquid 8 whose refractive index matches that of the contact lens material. The liquid may be contained in a bath vessel 9 of a size and shape such as to hold the immersed contact lens 1 in a fixed disposition while the active and reference beams are directed at it (as schematically represented at 10 and 11). Alternatively, the contact lens may be suspended in the liquid.

The hologram 6 can advantageously be provided over the full area, or at least the full visually used area, of the contact lens 1, thus avoiding the need for distinct near and far zones.

It will be appreciated that, although specifically described above by way of example in the bi-focal context, a contact lens having diffractive power can have other applications, for example to correct vision defects other than presbyopia. Further, a contact lens with diffractive power could be used to reduce chromatic aberration in normal vision (the normal eye usually involves about one dioptre of longitudinal colour) for example for sportsmen or soldiers.

Figure 5:
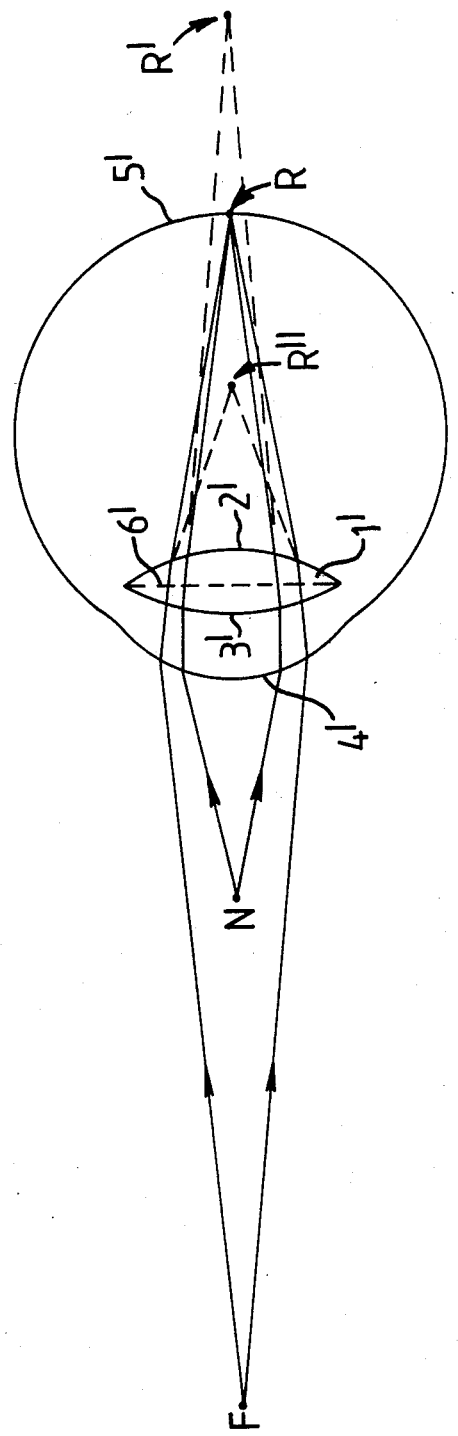

FIG. 5 is similar to FIG. 1 but schematically shows an artificial eye lens in the form of an implant lens which has been inserted within the eye in place of of the natural eye lens (as distinct from the contact lens of FIG. 1 which assists the natural eye lens).

Thus FIG. 5 schematically shows an implant lens 1' having a posterior surface 2' of given curvature and shape, and an anterior surface 3' of given shape and curvature related to that of the posterior surface 2' and the refractive index of the material of the lens and the aqueous and vitreous humours to provide suitable assistance and correction of the wearer's far vision. It will be understood that the lens is adapted to meet the particular requirements of the wearer so the posterior and anterior surfaces 2' and 3' may be of any desired curvature, e.g. spherical or toric, and the lens may be of any desired shape, e.g. with or without prism. For present purposes it is sufficient to consider the lens 1' as providing a basic refractive power appropriate for far vision of the wearer. Thus, light from a far object F is focussed by the implant lens 1' in conjunction with the wearer's cornea 4' to a position R on the retina 5'. The wearer can thus look at and see the far object F in focus.

However, since the wearer's vision lacks accommodation, the basic lens 1', being adapted to far vision, and the cornea 4' are of insufficient power to effect focussing on the retina of light from a near object N. As shown in broken line, light from such near object N would be focussed at a position R' spaced from and behind the retina 5'. To overcome this the implant lens 1' has a transmission hologram, schematically represented at 6', which provides the lens with diffractive power, equivalent to lens power, such that light from the near object N which is diffracted is focussed by the hologram 6' (in conjunction with the basic power of the implant lens 1' and the cornea 4') on to the retina 5'. The wearer can thus look at and see the near object N in focus by means of the light diffracted by the hologram.

As previously mentioned in relation to the hologram 6 of FIG. 1, and as more fully explained later, the hologram 6' may operate on a wavelength selective basis, or an amplitude selective basis, or a combination of both.

It will be understood that light which is not diffracted is transmitted through the hologram undeviated thereby. Such light from the near object N is focussed at the position R' behind the retina. However, since the position R' is spaced from the retina, the wearer's view of the near object N by way of the diffracted light is not unduly adversely affected by the undiffracted light. Conversely, when the wearer is looking at the far object F, light therefrom diffracted by the hologram becomes focussed (in conjunction with the action of the basic implant lens 1' and the cornea 4') at a position R" spaced from and in front of the retina 5', as shown in broken line. The wearer's focussed view when looking at the far object F is therefore by way of undiffracted light, and since position R" is spaced from the retina, this far view is not unduly adversely affected by the diffracted light.

Again, there should be a reasonable balance between the brightness of the far object F as viewed by way of the undiffracted light and the brightness of the near object N as viewed by way of the diffracted light.

It will thus be seen that the implant lens 1' incorporating the hologram 6' provides a bi-focal effect, the hologram constituting a holographic lens with diffractive power which adds to the basic power of the lens 1'. Although there is in principle no particular limit to the additional power which could be provided by the hologram, preferably it has a power up to about four dioptres thereby giving a near-add value from 0 to +4 dioptres.

Figure 6:
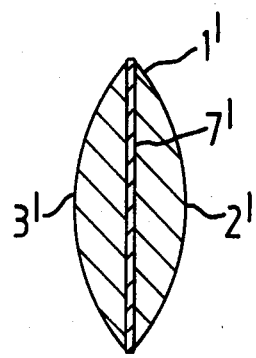
FIG. 6 is a schematic cross-section through an implant lens, FIG. 7 schematically illustrates a procedure for generating a hologram in an implant lens.

As shown schematically in FIG. 6, the implant lens 1' may have a layer 7' of photographic material, such as dichromated gelatin, within its volume and the hologram 6' may be formed in that layer 7'. Alternatively, however, the hologram 6' may be formed actually in the bulk material of the implant lens 1' if the material is suitable, or as mentioned later by surface relief on the bulk material. The bulk material of the implant lens may be tinted.

The hologram can be optically generated by active and reference beams, for example from a laser, directed at the implant lens effectively from conjugate point sources located so as to provide the required power in the resultant hologram in essentially the same manner as previously described in relation to the contact lens of FIGS. 1 to 4. These light, and preferably laser, beams interfere within the photosensitive material either in the layer 7' or the bulk of the implant lens.

If the active and reference beams are deliberately off-set to give an off-axis field of view for the hologram the implant lens is preferably shaped or marked to facilitate surgical insertion in the appropriate orientation.

Figure 7:
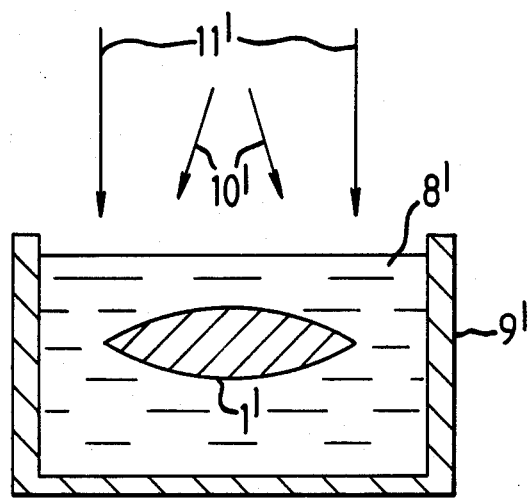

In order effectively to reduce the refractive power of the implant lens surface for the holographic generation procedure, the implant lens 1' can, as schematically shown in FIG. 7, be immersed in a liquid 8' whose refractive index matches that of the aqueous and vitreous humours. The liquid may be contained in a bath vessel 9' having a support (not shown) to hold the immersed implant lens 1' in a fixed disposition while the active and reference beams are directed at it (as schematically represented at 10' and 11').

Possible modes of operation of the hologram 6 or 6' will now be further explained with reference to FIG. 8 which graphically represents efficiency against wavelength.

Curve 100 represents the normal human visual response extending from the commonly called blue end of the visible spectrum to the red end.

Block 20 represents an idealistic transmission hologram which is wavelength selective with 100% efficiency. Thus, the hologram diffracts all the light over a selected wavelength band within the visible spectrum, but has no effect on light outside that selected wavelength band which is therefore transmitted through the hologram undeviated. The hologram may, for example, operate over a wavelength range covering between about one fifth and about one quarter of the visible spectrum, e.g. may be operative over a wavelength band of about 30 to 40 nanometers disposed around the green part of the visible spectrum. In the drawing block 20 is shown as having vertical sides which provide a specific wavelength cut-off as between 100% efficiency diffraction and zero efficiency. Such cut-off is probably impossible to achieve in practice and usually there would be a fall-off in efficiency with changing wavelength.

A more normal practical transmission hologram is represented by curve 30. This is shown as having its maximum efficiency, of about 60%, at a particular wavelength value and the efficiency falls off with change of wavelength from that value. Thus 60% of the light of the particular wavelength value is diffracted by the hologram while the other 40% is transmitted therethrough undeviated. The relative proportions of diffracted and undeviated light of other wavelengths vary as indicated by the curve.

Line 40 represents an idealistic non-wavelength selective transmission hologram, i.e. which diffracts with the same efficiency (shown in the drawing as about 40%) for all wavelengths. Thus, for light of any wavelength transmitted through the hologram, 40% is diffracted while the other 60% passes undeviated. In practice such a hologram is very difficult to make.

Usually a broad band hologram has some variation of efficiency with wavelength. Typically this may be as represented by curve 50 which shows the efficiency reducing to either side of a maximum value as the wavelength differs from that at which the maximum efficiency value applies. This hologram has diffractive power over all the visible spectrum (as has the idealistic non-wavelength selective hologram represented by line 40) but is of less than 100% efficiency. Thus, at all wavelengths within the visible spectrum, some light is diffracted on transmission through the hologram while other light passes through undeviated.

It will thus be understood that the hologram 6 or 6' may operate on a wavelength selective basis, as illustrated by block 20 in FIG. 8, or on an amplitude selective basis, as illustrated by line 40, or on a combined wavelength and amplitude selective basis as illustrated by curve 30, and may operate over the full visible spectrum with different efficiencies, e.g. varying from about 20% to about 40%, at different wavelengths, as illustrated by curve 50.

Referring again to FIGS. 1 and 5, it will be understood that wavelength selective operation means that light from the near object N within the wavelength band or bands over which the hologram operates is focussed on the retina, while light of other wavelengths is focussed at position R' and does not unduly adversely affect the view of the near object N. Light from the far object F within the wavelength band or bands over which the hologram operates is focussed at position R" and does not unduly adversely affect the view of the far object F by way of light of other wavelengths which is focussed on the retina. Amplitude selective operation means that a proportion of the light of a relevant wavelength from the near object N is focussed on the retina and a proportion is focussed at position R'. Similarly a proportion of the light of a relevant wavelength from the far object F is focussed at position R" and a porportion is focussed on the retina. In the case where the hologram is operative (at less than 100% efficiency) at all wavelengths within the visible spectrum, some light of any wavelength from the near object N is focussed on the retina and some at the position R', and some light of any wavelength from the far object F is focussed at R" and some on the retina. A combination of wavelength selection and amplitude selection means that some light from the near object N within the operative wavelength band or bands is focussed on the retina while some is focussed at position R' together with light of wavelengths outside the operative band or bands, and some light from the far object F within the operative wavelength band or bands is focussed at position R" while some is focussed on the retina together with light of wavelengths outside the operative band or bands. In all cases, the positions R' and R" are spaced from the retina so that light focussed at those positions is unfocussed at the retina and therefore does not unduly adversely affect the view by way of the light focussed on the retina.

It will be appreciated that a transmission hologram may be provided effectively to add power to the basic power of a basic artificial eye lens, as described above, or could be provided to give power to a basically powerless basic artificial eye lens. Further, a transmission hologram of negative power could be provided e.g. effectively to subtract power from the basic power of a basic artificial eye lens. Thus a bi-focal lens could have a basic power appropriate to near vision and an effectively negatively powered hologram for far vision. Yet further, if required a plurality of separately generated holograms of different powers (for example operative over different wavelength bands) could be incorporated in a single artificial eye lens. Although as explained above the hologram can advantageously be provided over the full area, or the full visually used area, of the lens, it could, if desired, be provided over part only of that area (and separately generated holograms could be provided over different respective, possibly overlapping, parts of the area).

Further, instead of generating the hologram optically as described above, mechanical generation may be employed. Thus, the hologram may take the form of a surface relief hologram, and may be mechanically generated, for example during moulding of the basic artificial eye lens. Thus the appropriate mould surface may be adapted, e.g. may have suitable grooves or ridges, to provide the required relief in the lens surface to form the hologram. Further, a mechanically generated hologram could be made to lie within the lens by forming it in two parts and joining them.

Yet further it will be appreciated that, although a transmission hologram is probably the most convenient way of imparting diffractive power to an artificial eye lens, it could be imparted in other ways such as forming a zone plate in analagous fashion to a diffraction grating.

I claim:

1. An artificial eye lens having basic refractive power providing one focus, and having diffractive power which deviates some light from the basic refractive power focus to another focus.

2. An artificial eye lens according to claim 1 in which the diffractive power is provided by a transmission hologram.

3. An artificial eye lens according to claim 1 or claim 2 having diffractive power over a particular wavelength band or bands so as to have a selective focussing action on light within that wavelength band or bands.

4. An artificial eye lens according to claim 1 or claim 2 having diffractive power of less than 100% efficiency such that a proportion of incident light of a relevant wavelength is diffracted while the remainder of the incident light of that wavelength is undeviated by diffraction.

5. An artificial eye lens according to claim 4 having some diffractive power over all or substantially all of the visible spectrum.

6. An artificial eye lens according to claim 5 having different efficiencies of diffractive power over different parts of the visible spectrum.

7. An artificial eye lens having a bi-focal action through basic power provided by the shape, curvature and material of the lens, and a different power provided through diffractive power.

8. An artificial eye lens according to claim 7 in which the basic power is for far vision and the diffractive power is additive to the basic power to provide a greater power for near vision.

9. An artificial eye lens according to claim 2 in which the hologram is provided over the full visually used area of the lens.

10. An artificial eye lens according to claim 2 in which the hologram is formed in a layer of the lens.

11. An artificial eye lens according to claim 10 in the form of a contact lens in which the hologram is formed in a surface layer of the lens.

12. An artificial eye lens according to claim 10 in the form of an implant lens in which the hologram is formed in a layer located within the lens.

13. An artificial eye lens according to claim 2 in which the hologram is formed in the bulk material of the lens.

14. An artificial eye lens according to claim 2 in which the hologram is optically generated by use of active and reference light beams.

15. An artificial eye lens according to claim 2 in which the hologram is a surface relief hologram.

16. An artificial eye lens according to claim 15 in which the hologram is mechanically generated during moulding of the lens.

17. An artificial eye lens according to claim 1 or claim 2 in which the bulk material of the lens is tinted.

18. An artificial eye lens according to claim 1 or claim 2 in the form of a contact lens.

19. An artificial eye lens according to claim 1 or claim 2 in the form of an implant lens.

20. An artificial eye lens according to claim 2 in which the hologram is formed on the bulk material of the lens.

21. An artificial eye lens which is basically powerless, the lens having a transmission hologram which gives it diffractive power.

22. An artificial eye lens according to claim 1 further defined in dividing light passing through a common portion thereof and providing said two foci for said light, a first portion of said light being focused by refraction and a second portion of said light being focused by diffraction.

23. An artificial eye lens according to claim 22 having an optical axis wherein said common portion is located on said axis.

24. An artificial eye lens dividing light passing through a common portion thereof and providing at least two foci for said light, each portion of said light being focused by diffraction.

* * * * *